United States Patent [19]

Loughlin

[11] Patent Number: 5,242,387
[45] Date of Patent: Sep. 7, 1993

[54] SUCTION-IRRIGATOR

[75] Inventor: Kevin R. Loughlin, Boston, Mass.

[73] Assignee: Brigham & Women's Hospital, Boston, Mass.

[21] Appl. No.: 880,386

[22] Filed: May 8, 1992

[51] Int. Cl.⁵ ............................................... A61M 3/00
[52] U.S. Cl. ...................................... 604/43; 604/33; 604/249; 604/323
[58] Field of Search .................... 604/27, 30, 33, 43, 604/246, 249

[56] References Cited

U.S. PATENT DOCUMENTS

| 1,696,018 | 12/1928 | Schellberg | 604/43 |
| 2,139,653 | 12/1938 | Belfrage | 604/39 |
| 4,149,315 | 4/1979 | Page, Jr. et al. | 604/249 |
| 4,402,310 | 9/1983 | Kimura | 604/30 |
| 4,676,778 | 6/1987 | Nelson, Jr. | 604/101 |

Primary Examiner—Randy C. Shay
Attorney, Agent, or Firm—Hamilton, Brook, Smith & Reynolds

[57] ABSTRACT

A suction-irrigator for use in endoscopic medical procedures having an elongate hollow body portion and a pair of valves in communication with the body to independently or concurrently admit irrigation fluid to the body and, hence, the patient, or to subject it to suction.

2 Claims, 2 Drawing Sheets

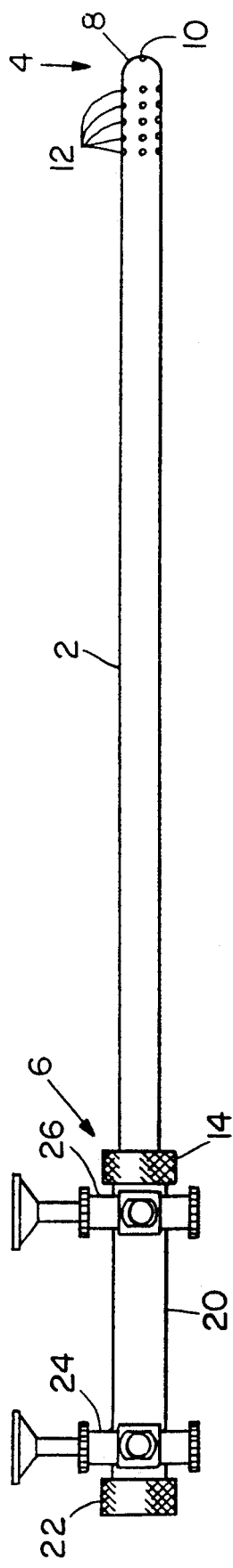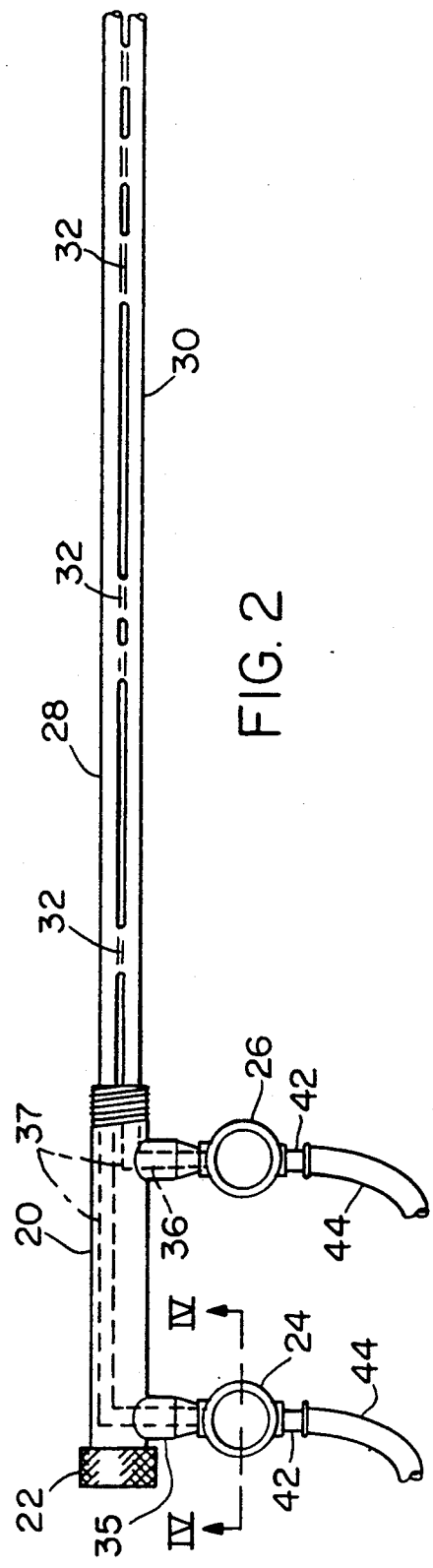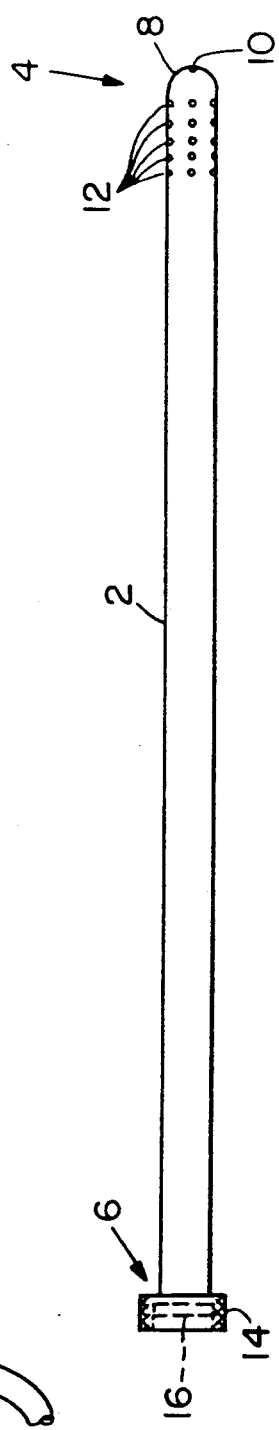

SUCTION-IRRIGATOR

BACKGROUND OF THE INVENTION

Endoscopic surgery has revolutionized a number of surgical procedures in specific areas. Joints, blood vessels, the abdomen and the chest all lend themselves well to this type of surgery.

Briefly, endoscopic surgery is performed with the surgeon observing his own actions on a video monitor. An external miniaturized video camera is attached by fiber optic tubes to a telescopic lens. A light source is combined and both are inserted into a patient through a small incision. In like manner, a surgeon operates with instruments held outside the patient and which extend into the operative field.

Endoscopic surgery performed in the abdomen is called laproscopic, and when performed in the chest is called thoracoscopic. These procedures often involve substantial amounts of bleeding. Unlike open surgery, there is little or no opportunity to employ a sponge to remove the blood. Accordingly, it has to be removed by a suction device. The instruments employed are generally elongate tubes attached to a source of vacuum which are inserted into a small incision.

Concurrently, it is often necessary to irrigate the operative field with sterile saline solution or the like. This means that one instrument must be removed from the patient and another inserted. This is not only traumatic to the patient but time consuming. It is to this problem that the present invention is directed.

SUMMARY OF THE INVENTION

The invention resides in a suction-irrigator for use in endoscopic procedures. It includes an elongate hollow body portion having a distal end and a proximal end. The distal end includes at least one exterior passageway orifice communicating with the interior of the body. Preferably there are a plurality of angularly spaced passageways extending a short distance from the distal end toward the proximal end. Preferably, one exterior passageway orifice is located at the apex of the closed rounded end of the distal portion of the body. A housing is removably secured to the proximal end of the body.

A pair of independent valves are secured to the housing and they are connected, one each, to a source of irrigation fluid and to a source of suction. Each valve is independently controlled to selectively and/or concurrently admit irrigation fluid into the hollow body or to subject the hollow body to vacuum.

The pair of elongate tubes extend lengthwise of the body portion in its interior into close proximity with the distal end where the exterior passageway orifices are located. The other end of the tubes are connected one each to the valves.

Each of the valves is a manually operated spring biased, normally closed, slide valve. One valve is connected to a source of vacuum and the other to a source of irrigating fluid, whereupon the surgeon may independently admit irrigating fluid into the hollow tube and out through the exit orifices to the field being irrigated, or apply suction independently of irrigation, or both, by manipulating one or both of the valves.

The above and other features of the invention including various and novel details of construction and combinations of parts will now be more particularly described with reference to the accompanying drawings and pointed out in the claims. It will be understood that the particular suction-irrigator embodying the invention is shown by way of illustration only and not as a limitation of the invention. The principles and features of this invention may be employed in varied and numerous embodiments without departing from the scope of the invention.

BRIEF DESCRIPTION OF THE DRAWINGS

FIG. 1 is a right side elevation of a suction-irrigator embodying features of the present invention.

FIG. 2 is a plan view of the suction-irrigator with portions removed to expose the interior.

FIG. 3 is a plan view of an elongate hollow body portion removed from the suction-irrigator.

DETAILED DESCRIPTION

Figure 4:
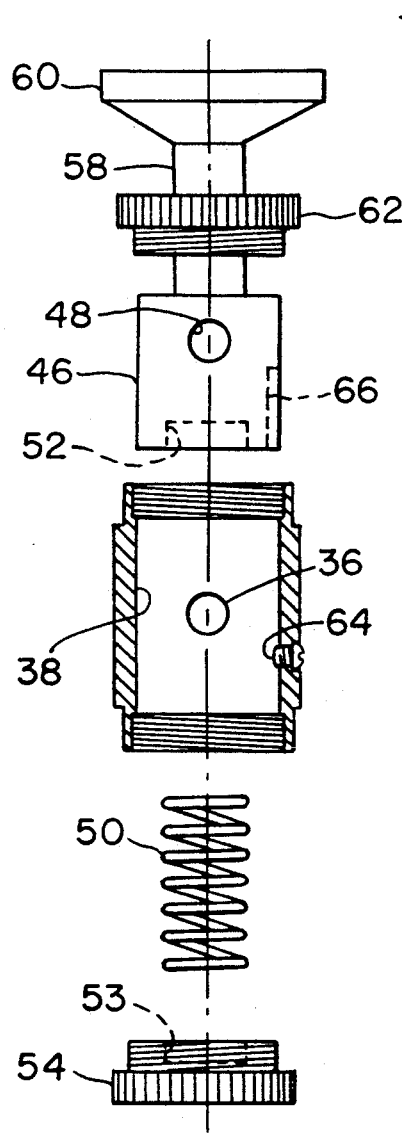
FIG. 4 is a sectional exploded view taken on the lines IV—IV of FIG. 2.

The suction-irrigator embodying the invention includes an elongate hollow body portion 2 having a distal end 4 and a proximal end 6. The body portion 2 is circular in cross section and the distal end 4 is a smoothly rounded dome 8. There is at least one external or exit passageway orifice 10 centrally located at the apex of the dome 8. A plurality of rows secondary orifices 12 are circumferentially arranged around the body portion near the dome 8. At the proximal end 6 of the body portion 2 is an exteriorally knurled, interiorally threaded, flange 14, containing a washer 16.

The threaded coupling flange 14 secures the body portion 2 removably to a housing 20 so that they may be removed for cleaning or sterilization or for the replacement of the hollow body with one of another size or with different sized orifices. The opposite end of the housing is closed by a threaded knurled cap 22.

A pair of spring biased, manually operated slide valves 24, 26 are secured with the housing 20 and communicate, respectively, to elongate tubes 28 and 30 which extend outwardly to close the distal end of the body portion 2. The tubes are secured to one another at points 32 for strength.

Valves 24 and 26 are identical and, as seen in FIGS. 2 and 4, each valve includes a connector 35 having a central passageway 36 which communicates with the one of tube 28 or 30 by way of conduits 37 in the housing 20. The passageway 36 is in communication with a cylinder 38 which, in turn, has a second passageway not seen in FIG. 4 which communicates with a nipple 42 (FIG. 2) to which a flexible tube 44 is attached.

One flexible tube 44 is connected to a source of vacuum or suction and the other to a source of pressurized irrigating fluid.

A piston 46 is located for sliding movement in the cylinder 38 and has a transaxial bore 48 passing through it. A spring 50 is received within a recess 52 in the piston 46 and biases the piston upwardly in the cylinder 38. The spring 50 is seated in a recess 53 in a threaded knurled cap 54 which threads into the bottom of the cylinder 38.

Extending upwardly from the piston 46 is a plunger 58 in the form of a valve stem terminating in a truncated cone 60 for engagement by a surgeon or assistant's finger. The upper end of the cylinder is closed by a threaded cap 62. A detent 64 in the cylinder is engageable in a slot 66 in the piston to assure that the bore 48 will line up with the passageway 36.

Assume the surgeon wishes to irrigate, the spring 50 normally biases the piston 46 upwardly to maintain the valve in closed position. When he or his assistant depresses the plunger 58, the transverse passageway 48 in the piston becomes aligned with the opening 36 to place the valve in communication with the supply of irrigating fluid to fill the body 2 and to irrigate the surgical field. If he wishes to suction blood, the other valve is opened, depressurizing the system and to apply suction through the orifices 10 and 12 to draw blood from the field into the body 2.

I claim:

1. A suction-irrigator for use in medical procedures comprising:
   an elongate hollow body portion having a distal end and a proximal end;
   a hollow dome formed at the distal end;
   at least one exterior passageway orifice in the hollow dome at the distal end communicating with the interior of the body portion through which passageway irrigation fluid may both pass out of the hollow body and reenter the hollow body;
   a housing removably secured to the proximal end of the body;
   a pair of halves secured to the housing and connected one each, to a source of irrigation fluid and to suction to selectively alone or concurrently admit irrigation fluid into the hollow body or subject said body to suction; and
   a pair of tubes connected, one each, to one of said valves and extending inwardly of the hollow body portion and terminating in close proximity with the hollow dome at the distal end such that the hollow body is a receptacle for irrigation fluid both before and after the fluid passes from and reenters the irrigator.

2. A suction-irrigator according to claim 1 wherein there are a plurality of rows of orifices circumferentially arranged around the body portion near the dome.

* * * * *

UNITED STATES PATENT AND TRADEMARK OFFICE
CERTIFICATE OF CORRECTION

PATENT NO. : 5,242,387
DATED : September 7, 1993
INVENTOR(S) : Kevin R. Loughlin It is certified that error appears in the above-indentified patent and that said Letters Patent is hereby corrected as shown below:

Column 4, line 13, claim 1, change "halves" to read --valves --.

Signed and Sealed this

Twenty-second Day of March, 1994

Attest:

BRUCE LEHMAN

*Attesting Officer*     *Commissioner of Patents and Trademarks*